United States Patent [19]

Sauer et al.

[11] Patent Number: 5,901,195

[45] Date of Patent: May 4, 1999

[54] TWO-STEP RADON INVERSION PROCESSING FOR φ-PLANES HAVING LOCAL RADON ORIGINS

[75] Inventors: Frank Sauer; Supun Samarasekera, both of Princeton; Kwok Tam, Edison, all of N.J.

[73] Assignee: Siemens Corporate Research, Inc., Princeton, N.J.

[21] Appl. No.: 08/940,324

[22] Filed: Sep. 30, 1997

[51] Int. Cl.$^6$ ........................................... A61B 6/03
[52] U.S. Cl. ................................. 378/4; 378/901
[58] Field of Search ................... 378/4, 901; 382/131

[56] References Cited

U.S. PATENT DOCUMENTS

| | | | |
|---|---|---|---|
| 5,257,183 | 10/1993 | Tam | 378/4 |
| 5,365,560 | 11/1994 | Tam | 378/8 |

OTHER PUBLICATIONS

"Zeugmatography By Reconstruction From Projections", Lauterbur et al., IEEE Transactions on Nuclear Science, vol. NS–27, No. 3, Jun. 1980, pp. 1227–1231.

*Primary Examiner*—David Vernon Bruce
*Attorney, Agent, or Firm*—Lawrence C. Edelman

[57] ABSTRACT

A two-step 3D Radon inversion processor for processing Radon data on a set of vertically oriented co-axial φ-planes that partition Radon space, wherein each of the φ-planes is sampled during the processing so as to have its own independent local Radon origin. In accordance with further principles of the present invention, a 3D Radon data generator generates Radon data on a set of vertically oriented co-axial φ-planes that partition Radon space, wherein each of the φ-planes is sampled so as to have its own independent local Radon origin, and a two-step 3D Radon inversion processor independently processes each of the φ-planes. Any shift of the local Radon origins with respect to a global coordinate system is compensated for during the 3D Radon inversion processing. Compensation for the origin shift may be made during or after a first step of the Radon inversion processing.

7 Claims, 3 Drawing Sheets

200 RADON SPACE (r, θ, φ)

206 INTERMEDIATE SPACE (r', φ, z)

210 OBJECT SPACE (x, y, z)

TWO-STEP RADON INVERSION PROCESSING FOR φ-PLANES HAVING LOCAL RADON ORIGINS

BACKGROUND OF THE INVENTION

1. Field of the Invention

The present invention relates generally to Radon inversion processing, and more specifically to two-step Radon inversion processing where Radon data is sampled into φ-planes sample grids having independent local Radon origins. The invention is particularly useful in computed tomographic (CT) imaging apparatus that performs three-dimensional (3D) image reconstruction.

2. Description of the Background Art

Recently a system employing cone beam geometry has been developed for three-dimensional (3D) computed tomographic (CT) imaging that includes a cone beam x-ray source and a 2D area detector. An object to be imaged is scanned, preferably over a 360° angular range and along its length, by any one of various methods wherein the position of the area detector is fixed relative to the source, and relative rotational and translational movement between the source and object provides the scanning (irradiation of the object by radiation energy). The cone beam approach for 3D CT has the potential to achieve 3D imaging in both medical and industrial applications with improved speed, as well as improved dose utilization when compared with conventional 3D CT apparatus (i.e., a stack of slices approach obtained using parallel or fan beam x-rays).

As a result of the relative movement of the cone beam source to a plurality of source positions (i.e., "views") along the scan path, the detector acquires a corresponding plurality of sets of cone beam projected measurement data (referred to hereinafter as measurement data), each set of measurement data being representative of x-ray attenuation caused by the object at a respective one of the source positions. After acquisition, the measurement data is processed for reconstructing a 3D image of the object.

As compared with the processing required for reconstructing an image when using an x-ray source supplying parallel or fan beams, the processing of the measurement data acquired when using a cone beam source is computationally much more complex. This is because when using a parallel or fan beam source, the measurement data is already directly representative of a 2D Radon transform of a cross-section of the object. However, this is not the case when using a cone beam source. Processing of the measurement data acquired using a cone beam source comprises:

1) conversion of the measurement data to Radon derivative data. This may be accomplished using the techniques described in U.S. Pat. No. 5,257,183 entitled METHOD AND APPARATUS FOR CONVERTING CONE BEAM X-RAY PROJECTION DATA TO PLANAR INTEGRAL AND RECONSTRUCTING A THREE-DIMENSIONAL COMPUTERIZED TOMOGRAPHY (CT) IMAGE OF AN OBJECT issued Oct. 26, 1993, hereby incorporated by reference, 2) conversion of the Radon derivative data to Radon data at polar grid points using, for example, the technique described in U.S. Pat. No. 5,446,776 entitled TOMOGRAPHY WITH GENERATION OF RADON DATA ON POLAR GRID POINTS issued Aug. 8, 1995, also hereby incorporated by reference, and 3) performing an inverse 3D Radon transformation of the Radon data using known techniques, such as those described in detail in the forenoted U.S. Pat. No. 5,257,183 for reconstructing image data that, when applied to a display, provides a view of the 3D CT image of the object.

Although the theory for exactly reconstructing an image using cone beam measurement data is generally known, such as from the U.S. patents noted above, a practical implementation of the processing turns out to be quite problematic. Not only is the amount of measurement data to be processed very large and rapidly acquired in accordance with a timing that is mainly determined by the geometry of the scan path, but the calculations required on the acquired data are quite complex. For example, if one decides to reconstruct an object with $200\times200\times200=8.10^6$ voxels (voxel=volume element of the object), for good quality one needs to obtain the object's 3-D Radon transform with a multiple amount (e.g., 4) of Radon samples, i.e., $32.10^6$ samples, and then perform the Radon inversion. The most computationally expensive part of the object reconstruction is the calculation of the Radon derivative data (step 1 noted above). As noted in the above U.S. patents, as well as in detail in U.S. Pat. No. 5,463,666 entitled HELICAL AND CIRCLE SCAN REGION OF INTEREST COMPUTERIZED TOMOGRAPHY issued Oct. 31, 1995, hereby incorporated by reference, for calculating the value of the Radon data at a given Radon sample point, it is typically necessary to process the measurement data acquired from several source positions, with the measurement data from each source position developing a contribution to the final value for that sample point by way of data combination. Thus one needs to calculate about $100.10^6$ line integral derivatives. Each line integral derivative requires the calculation of $200.10^6$ single line integrals, since one uses the difference between two closely spaced line integrals to calculate a single line integral derivative. However, before one can perform these line integral derivative calculations, one has to compute for each Radon sample which source positions will provide the measurement data that must be processed, and determine the lines on the measurement data along which the integration must be performed. These latter determinations involve highly nonlinear calculations and are therefore computationally costly. In order to compute the contributing source positions, one has to intersect the source scanning path with the Radon integration plane as explained in the forenoted U.S. Pat. No. 5,463,666. When using a spiral scan path, this requires the solution of transcendental equations, which are computationally expensive. Furthermore, in addition to determining the lines on the measurement data along which the integration must be performed, one also has to calculate the appropriate end points of those lines for data combination purposes and region-of-interest masking. The complexity of these above-noted calculations leads to severe bottlenecks in processing of the measurement data, so as to prevent rapid and efficient image reconstruction.

In U.S. patent application Ser. No. 08/940,924 entitled A PRE-CALCULATED HITLIST FOR REDUCING RUN-TIME PROCESSING OF AN EXACT CONE BEAM RECONSTRUCTION ALGORITHM, filed contemporaneously herewith, a method and apparatus is described in which before operation of a cone beam imaging apparatus for acquiring and processing of measurement data to reconstruct an image of an object, information required for processing of the acquired measurement data is pre-calculated and stored. The pre-calculated information is then used during the imaging operation of the cone beam apparatus for processing of the acquired measurement data to reconstruct an image of the object. The pre-calculated image reconstruction information is organized into what is referred to as a "hitlist". In general, the hitlist contains processing information that is determined primarily by geometric parameters of the imaging apparatus that are already predetermined during its imaging operation, such as the pitch and other parameters of the source/detector scan path, the object dimensions, the detector resolution, and a desired sampling of the scan path and the Radon space. The hitlist includes processing information indicating the correspondence between points in Radon space and the source positions that contribute thereto, parameters that define the line integrals that need to be calculated in the measurement data acquired at each of the source positions, as well as other information useful for image reconstruction processing.

Although calculation of the hitlist information is computationally expensive, since the information in the hitlist must be calculated anyway in order to process each set of the acquired measurement data during imaging operation of the apparatus, its pre-calculation provides a very significant speed-up of the run-time (image) processing of the measurement data and results in a greatly improved efficiency in the implementation of the image reconstruction algorithm. However, as described in more detail in the forenoted U.S. patent application Ser. No. 08/940,924, since hitlist information is required for each of the many points in Radon space that define the objects region of support, the size of the hitlist is actually quite large. For example, as previously noted, approximately $100 \times 10^6$ line integral derivative calculation are required. If the image reconstruction processing information stored in the hitlist comprises 24 bytes to describe the processing for determining each Radon point, then 2.4 Gbytes of memory is required.

In U.S. patent application Ser. No. 08/940,489 entitled A REDUCTION OF HITLIST SIZE IN A SPIRAL CONE BEAM CT BY USE OF LOCAL RADON ORIGINS, filed contemporaneously herewith, a method and apparatus is described in which a symmetry is induced in the reconstruction processing so that reconstruction processing information contained in the hitlist and calculated on less than all of a set of vertically oriented co-axial φ-planes that partition the Radon space, is re-used for calculating Radon data for other ones of the φ-planes that partition the Radon space. The induced symmetry establishes a correspondence between the points in Radon space and the source positions, thereby allowing re-use of the reconstruction information calculated on only one of the φ-planes. In accordance with that invention, this is accomplished by establishing on each of successive ones of the φ-planes an independent local Radon origin. The Radon origin for each of the successive φ-planes are shifted an amount corresponding to an amount of z-axis shift that a projection of the spiral scan path experiences from its position in the immediately prior one of the successive φ-planes.

The present invention is directed to a method of processing Radon data having such independent Radon origins.

SUMMARY OF THE INVENTION

In accordance with the principles of the present invention, a two-step 3D Radon inversion processing is provided for processing Radon data on a set of vertically oriented co-axial φ-planes that partition the Radon space, wherein each of the φ-planes is sampled during the processing so as to have its own independent local Radon origin. Any shift of the local Radon origins with respect to a global coordinate system is compensated for during the 3D Radon inversion processing.

In accordance with further principles of the present invention, a Radon data generator generates Radon data on a set of vertically oriented co-axial φ-planes that partition Radon space, wherein each of the φ-planes is sampled so as to have its own independent local Radon origin, and a two-step 3D Radon inversion processor independently processes each of the φ-planes. Any shift of the local Radon origins with respect to a global coordinate system is compensated for during the 3D Radon inversion processing.

In accordance with one aspect of the invention compensation for the origin shift is made during a first step of the Radon inversion processing, by backprojecting the Radon data from the φ-planes onto φ-plane sample grids (z,r') which are not shifted, i.e., are accordingly offset, from the local Radon origins. Thus, the sample grids (z,r') are already aligned with the global grid. The offset of the Radon origins is taken into account by introducing a corresponding offset into coordinate variables that define this first step of the Radon inversion.

In accordance with an alternative aspect of the invention, in the first step one backprojects onto φ-plane sample grids (z,r') which are shifted along with the local Radon origins, and then, before performing the second step of the two-step inversion processing (i.e., 2D Radon inversion in the z-planes), shifting the backprojection results a corresponding amount toward the global origin to compensate for the previous shift in the local Radon origins. This shifting of the backprojection results is accomplished by interpolating them onto a new grid which is aligned with the global coordinate system.

One environment in which the invention is particularly useful is in the arrangement of the forenoted patent application Ser. No. 08/940,489.

DETAILED DESCRIPTION OF THE PREFERRED EMBODIMENTS

Figure 1:
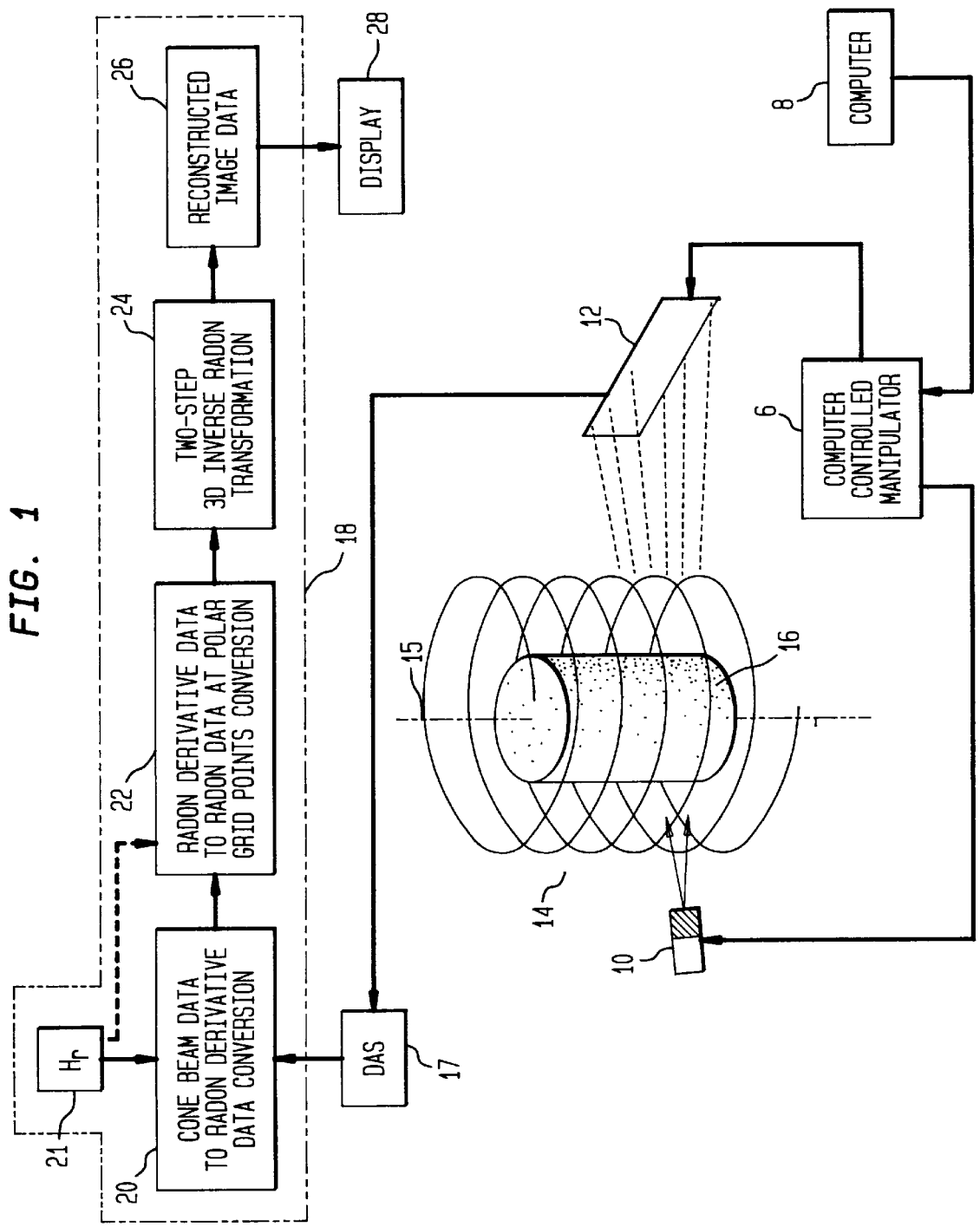
FIG. 1 is a block diagram and simplified perspective illustration of the imaging of an object using a cone beam imaging apparatus, wherein the apparatus uses a pre-calculated hitlist of reconstruction processing information for processing acquired measurement data in accordance with the principles of the present invention.

FIG. 1 illustrates a cone beam 3D CT imaging apparatus that operates in accordance with the principles of the present invention. Except as to be specifically described later with respect to implementation of image reconstruction processing in accordance with the present invention, the illustrated imaging apparatus is constructed and operates substantially the same as described in the forenoted U.S. Pat. Nos. 5,257,183 and 5,446,776.

Briefly, referring again to FIG. 1, a computer controlled manipulator 6, in response to control signals from an appropriately programmed computer 8, cause a source 10 of cone beam energy (such as x-rays) and a two-dimensional array detector 12 to cooperate (scan) at a plurality of discreet, sequentially occurring adjacent source positions, along a predefined source scanning path, illustrated as a spiral scan path 14 centered on a predetermined axis 15 of an object 16. As a result of the source/detector cooperation, detector 12 acquires complete cone beam measurement data which is then used for reconstructing an image of object 16. Although source 10 is shown as an x-ray source, other types of imaging energy might be useful, such as neutrons, positrons, etc.

Computer 6, manipulator 8, source 10 and detector 12 cooperate to accomplish scanning of the object in a manner generally well understood by those skilled in this art, i.e., such as described in detail in the forenoted U.S. Pat. No. 5,463,666, and therefore discussion of further details of this portion of the operation of the cone beam imaging apparatus is deemed not necessary.

After the x-ray energy passes through the field of view of the imaging apparatus, measurement signals corresponding to the sensed x-ray energy falling on elements within detector 12 are supplied to a data acquisition system (DAS) 17 which, like the previously described portions of FIG. 1, may operate in a fashion well known to those of ordinary skill in this technology for digitizing, pre-processing, and storing of measurement data corresponding to the acquired measurement signals.

The cone beam measurement data from the DAS 17 is supplied to a buffer memory and image reconstruction processor 18, which may be a computer programmed to perform various data conversions that process the measurement data so as to reconstruct an image, generally illustrated by the blocks within processor 18. More specifically, at block 20 the measurement data is processed so as to be converted to Radon derivative data. A spherical coordinate system $(r,\theta,\phi)$ is preferably used to facilitate the Radon inversion processing. This may be accomplished, in general, using the techniques described in the forenoted U.S. Pat. No. 5,257,183. However, as will be described in greater detail later, the speed and efficiency of this portion of the image reconstruction processing is improved over the techniques described in the forenoted U.S. Pat. No. 5,257,183, by use of a "relative" hitlist ($H_r$) of pre-calculated image reconstruction processing information that is stored in a database 21, and used during run-time (imaging) operation of the apparatus for processing the acquired measurement data to reconstruct an image of the object.

Figure 5:
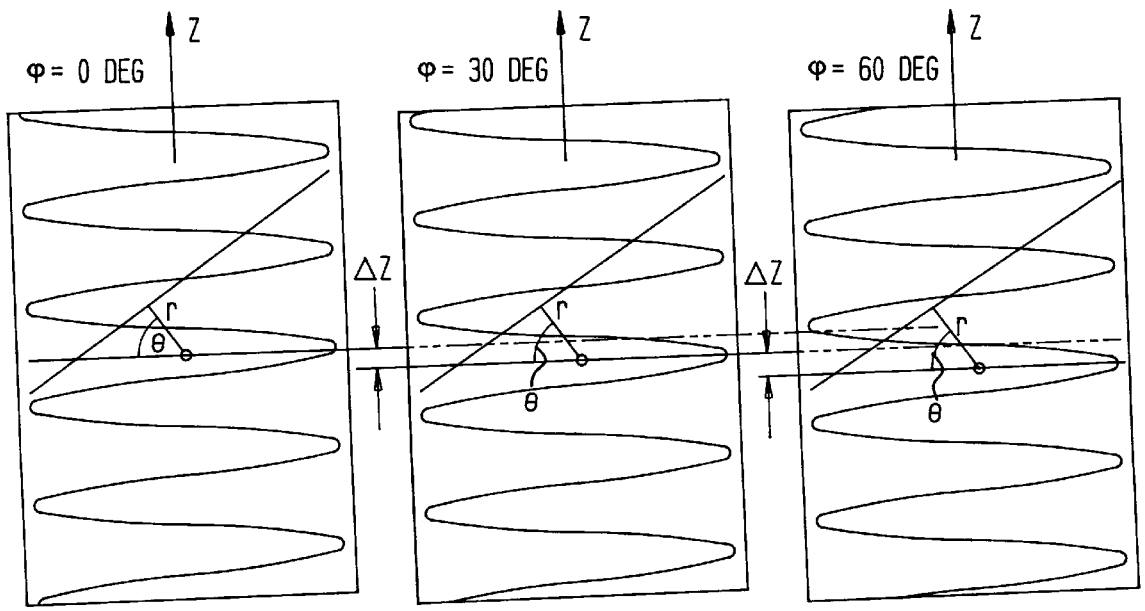
FIG. 5 illustrates use of local Radon origins for the successive φ-planes of FIG. 4, for inducing a symmetry into the determinations illustrated therein, thereby allowing re-use of pre-calculated image reconstruction processing information.

At block 22 the Radon derivative data is converted to Radon data at equally spaced polar grid points using, for example, the technique described in detail in conjunction with FIG. 5 of the forenoted U.S. Pat. No. 5,446,776. Briefly, as described therein, the Radon derivative data from block 20 is converted to Radon derivative data at equally spaced polar grid points using nearest neighbor or interpolation techniques, and then summed to develop the Radon data at equally spaced polar grid points. The hitlist of reconstruction processing information stored in database 21 preferably also provides pre-calculated information during this portion of the reconstruction processing, such as weighting information used for interpolation processing (as indicated by a dashed line from block 21 to block 22), thereby further improving the speed and efficiency of this portion of the reconstruction processing.

Figure 2:
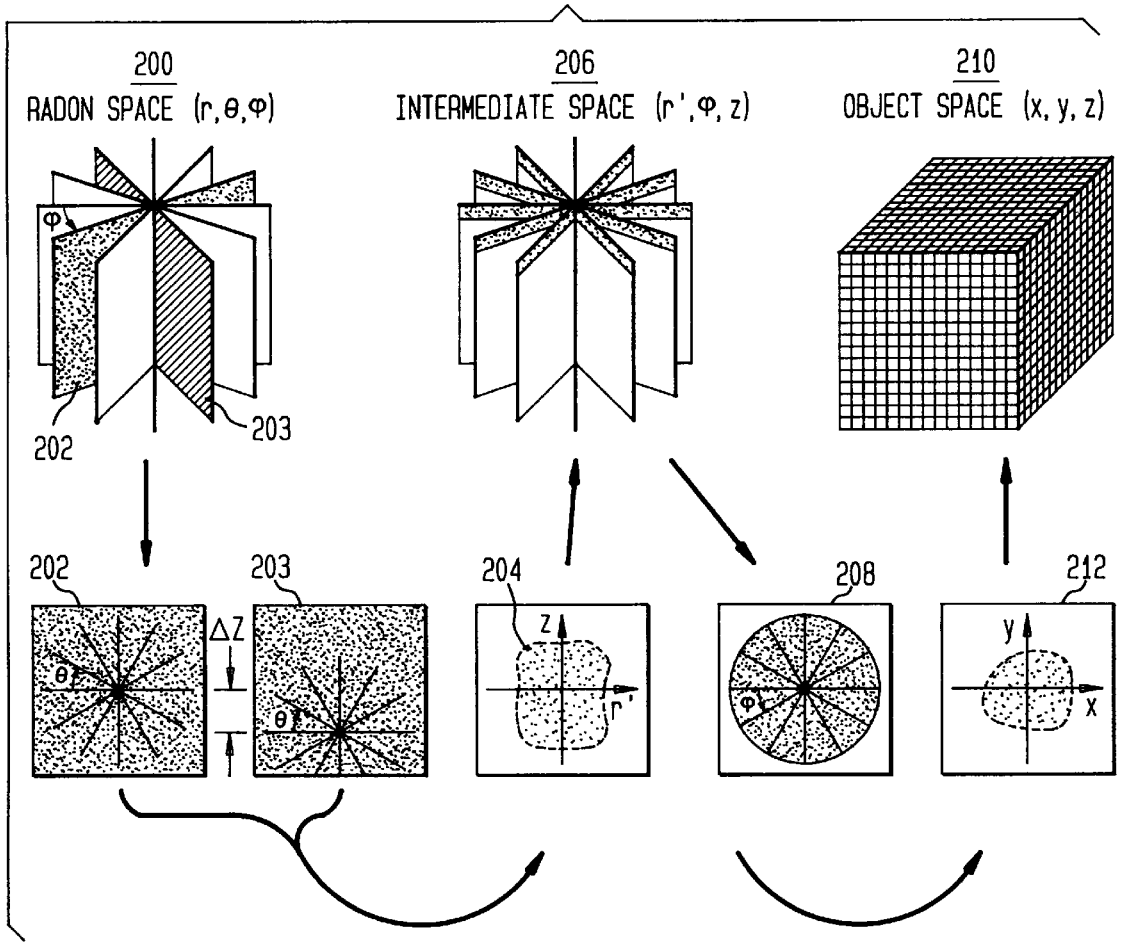
FIG. 2 illustrates 3D inverse transformation processing of 3D Radon data having independent local Radon origins in accordance with the present invention, for developing image data for reconstructing an image of the object.

At block 24 the Radon data is subjected to inverse 3D Radon transformation processing in accordance with the principles of the invention. FIG. 2 generally illustrates one example of such two-step 3D Radon inversion processing. The two-step 3D Radon inversion processing of block 24, except for modification in accordance with the present invention, which will be described later, is generally known and described, for example, in the forenoted U.S. Pat. No. 5,257,183. Briefly, one starts with the Radon data from block 22, sampled in a Radon space 200 that is defined by a spherical coordinate system $(r,\theta,\phi)$, with two p-planes 202 and 203 of a plurality of vertically oriented coaxial $\phi$-planes being illustrated with a polar grid coordinate thereon. As will be described later, origin of the sample grid of each of the $\phi$-planes are independent of one another.

In the first reconstruction step, 2-D Radon inversions are performed on the Radon data in each of the $\phi$-planes using a procedure such as filtered backprojection. Each $\phi$-plane will then contain a 2-D projection image, such as 204, of the object for the corresponding viewing angle, sampled in the Cartesian coordinate system (r',z). After the first 2D inversion, information about the whole object is contained in the cylindrical coordinate system 206 (r',$\phi$,z). In the second reconstruction step, horizontal planes (z-slices) 208 parallel with the z axis are defined in system 206 and data descriptive of a 3D image of the object is developed in object space 210 slice-by-slice. More specifically, for each z-slice 208, a 2D CT reconstruction procedure, such as filtered backprojection, operates on the values of the 2D projection images in the plane of the z-slice, thereby calculating a 2D image 212 of the object for each z-slice. The final result is image data representative of the spatial distribution of the 3D object, sampled in the Cartesian coordinate system (x,y,z).

The image data developed thereby is stored at block 26 and then fed from reconstruction processor 18 to a display 28, which may operate in known fashion, to provide a 3D CT view of object 16.

Except for modification of the inverse 3D Radon transformation processing in accordance with the present invention, a more detailed description of the blocks of FIG. 1 can be found in the forenoted patents incorporated by reference herein.

As previously noted, and as described in detail in the forenoted U.S. patent application Ser. No. 08/940,924, before operation of a cone beam imaging apparatus for acquiring and processing of measurement data to reconstruct an image of an object, information required for processing of the acquired measurement data is pre-calculated and stored in database 21. The pre-calculated information is then used during the imaging operation of the cone beam apparatus for processing of the acquired measurement data to reconstruct an image of the object. The pre-calculated image reconstruction information is sometimes referred to as a "hitlist". In general, the hitlist contains processing information that is determined primarily by geometric parameters of the imaging apparatus that are predetermined during its imaging operation, such as the pitch and other parameters of the source/detector scan path, the dimensions of the object, the detector resolution, and a desired sampling of the scan path and the Radon space. The hitlist includes processing information indicating the correspondence between points in Radon space and the source positions that contribute thereto, parameters that define the line integrals that need to be calculated in the measurement data acquired at each of the source positions, as well as other information useful for image reconstruction processing.

Pre-calculation of the hitlist information provides a very significant speed-up of the run-time (image) processing of the measurement data and results in a greatly improved efficiency in the implementation of the image reconstruction algorithm. However, as described in more detail in the forenoted U.S. patent application Ser. No. 08/940,924, since hitlist information is required for determining data for each of the many points in Radon space that define the objects region of support, the size of the hitlist is actually quite large.

Figure 3A:
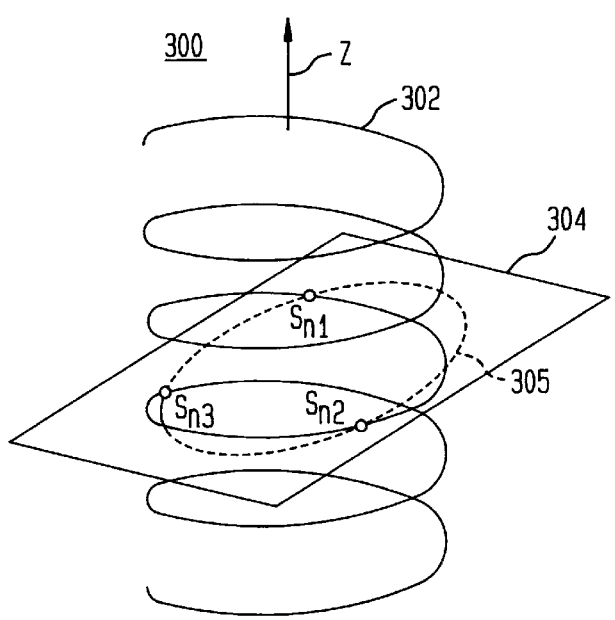
FIGS. 3a and 3b illustrate determination of the source positions which contribute to a given Radon sample point.
Figure 3B:
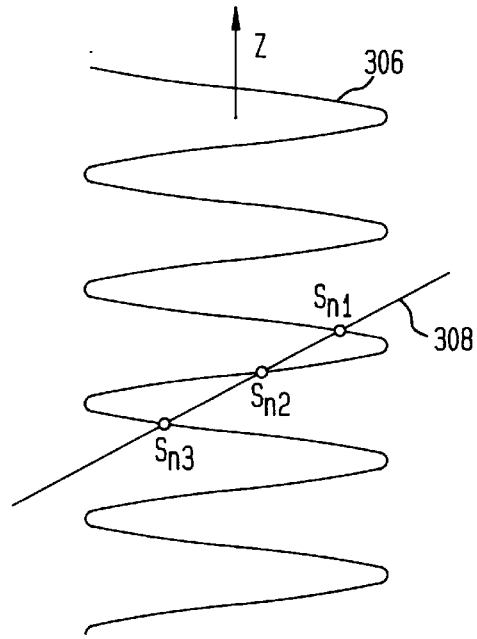
Figure 4:
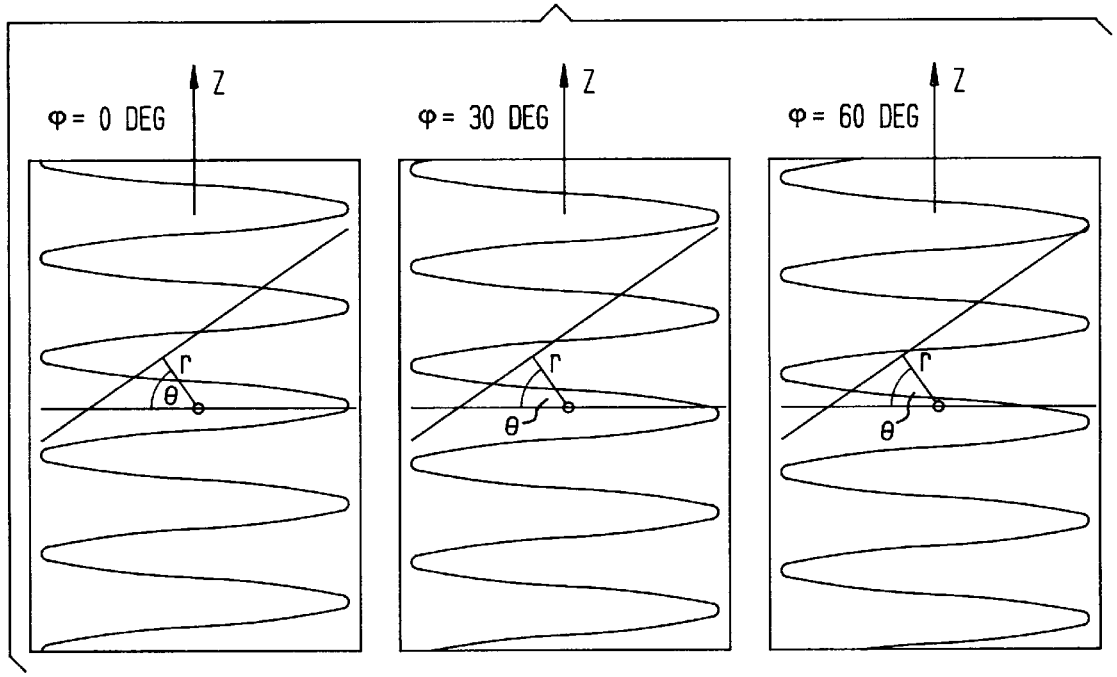
FIG. 4 illustrates determination of the source positions which contribute to a Radon sample point which is similarly positioned on selected ones of successive φ-planes in Radon space.

Before description of the novel inverse 3D Radon transformation processing in accordance with the present invention, the reader is referred to FIGS. 3–5 for some additional background information.

FIG. 3 illustrates determination of the source positions $S_{n1}$, $S_{n2}$ and $S_{n3}$ along scan path 302 which acquire measurement data to be processed for contributing to a given Radon sample point. As well known by those skilled in this art, 3D Radon transform datum at a given point $(r,\theta,\phi)$ can be uniquely determined by the planar integral of the object's x-ray attenuation coefficient, with the integration plane determined by the vector $(r,\theta,\phi)$, not specifically shown. The measurement data acquired by the detector at source positions which lie on the integration plane contribute to the particular Radon value. FIG. 3a depicts this situation in 3D. The illustrated exemplary integration plane 304 intersects a the spiral scan path 302 at positions $S_{n1}$, $S_{n1}$ and $S_{n3}$. The intersections lie on an ellipse, shown by dashed line 305, which is generated by projecting the spiral in the z-axis direction onto integration plane 304. To calculate the source intersections, one merely projects both scan path 302 and integration plan 304 into the φ-plane (determined by the φ-coordinate of the Radon point), as shown in FIG. 3b. Then, one merely has to solve the 2-D problem of intersecting a sine-function 306 (projection of spiral 302) with a line 308 (projection of plane 304) to determine the position of points $S_{n1}$, $S_{n2}$ and $S_{n3}$. Finally, one translates these positions back into 3D space based on knowledge of the geometry of scan path 302. This procedure is repeated until source position information is developed for all the Radon points that are desired for reconstructing an image of the object with a desired resolution.

FIG. 4 illustrates determination of the source positions which contribute to Radon sample points which are similarly positioned on selected ones of successive φ-planes (0°, 30° and 60°) in Radon space, i.e., Radon sample points which have the same r and θ coordinates. As shown thereby, as we move from φ-plane to φ-plane while keeping r and θ constant, the spiral's projection shifts along the z-axis, which results in new intersections, related to the previous ones in a highly nonlinear way. When one stores these results in the hitlist, one needs separate, unique, entries for the Radon sample points of each φ-plane. For a more detailed description, the reader is referred to the forenoted U.S. Pat. No. 5,257,183 (FIGS. 3–10), or the forenoted U.S. patent application Ser. No. 08/940,924.

The forenoted U.S. patent application Ser. No. 08/940,489 describes a technique that allows the hitlist entries calculated for the Radon sample points on one φ-plane to be re-used for the similarly positioned Radon sample points in other ones, and in fact all of the other ones, of the φ-planes. A visual illustration of this technique is shown in FIG. 5. As shown therein, the Radon origin on each of successive ones of the φ-planes (with only φ-planes 0°, 30° and 60° being illustrated) is shifted by an amount (Δz) corresponding to the amount of z-axis shift that the projection of the spiral path 302 experiences between the successive φ-planes. The ΔZ illustrated in FIG. 4 corresponds to Δz times the number of φ-planes between 0° and 30°.

As a result of the origin shift for successive φ-planes, the intersections between the projections of the spiral and the integration plane are the same in the local coordinate systems of each φ-plane. Consequently, the same source positions, in a relative sense, contribute to a given r,θ Radon position independent of the φ-plane, and the reconstruction information in the hitlist intended for a given φ-plane can now be re-used for determining Radon data in any of the successive φ-planes. However, now there is a shift in the Radon origins of the φ-plane data that needs to be taken account of.

In accordance with a the principles of the present invention, the two-step Radon inversion processing of block 24 of FIG. 1, is modified to allow one to establish a sample grid on each of the φ-planes containing the Radon transform data, a local Radon origin, which local origin is independent of the local origin of each of the other ones of the φ-planes. The shifting of the local Radon origins of the Radon space φ-planes with respect to a global coordinate system can be compensated for during Radon inversion processing.

More specifically, the compensation can be made during the first step of the Radon inversion processing shown in FIG. 2, by backprojecting the Radon data (from the φ-planes) onto sample grids (z,r') which are not shifted, i.e., are accordingly offset, from the local Radon origins. This offset is shown as ΔZ in the space between φ-planes 202 and 203 in FIG. 2, where ΔZ=the total shift of the origin in the z-axis direction between φ-planes 202 and 203. Thus, the sample grids are already aligned in the z-axis direction and as such are part of a global sample grid. Consequently, the z-axis offset of the Radon origins is taken account of by introducing a corresponding z-axis delta into the coordinate variables during this step of the Radon inversion processing.

Alternatively, in accordance with another aspect of the invention, one can backproject onto z,r' sample grids which are shifted along with the local Radon origins, and then, before performing the second step of the inversion processing (2D Radon inversion in the z-planes), shifting the backprojection results a corresponding amount toward the global origin to compensate for the previous shift in the local Radon origins. This shifting of the backprojection results is accomplished by interpolating them onto a new sample grid which is aligned with the global coordinate system.

Thus, there has been shown and described a novel method and apparatus for processing Radon data on a set of vertically oriented co-axial p-planes that partition the Radon space, wherein φ-planes can be accommodated that each have their own independent local Radon origin. Many changes, modifications, variations and other uses and applications of the subject invention will, however, become apparent to those skilled in the art after considering this specification and its accompanying drawings, which disclose preferred embodiments thereof. For example, although a z-axis shift is shown in the illustrated embodiments, an arbitrary Radon origin shift, such as Δr,Δθ is allowable and can be compensated. Furthermore, although inversion by backprojections is shown, other types of inversion are possible, such as on using FFT techniques. All such changes, modifications, variations and other uses and applications which do not depart from the general teaching of the invention herein, are deemed to be covered by this patent, which is limited only by the claims which follow as interpreted in light of the foregoing description.

What is claimed is:

1. A method of operating a 3D CT imaging apparatus having a cone beam radiation source and detector arrangement, for reconstructing an image of an object that is scanned by said source and detector arrangement, comprising the following steps:

operating said source and detector arrangement at a plurality of source positions along a scan path that traverses the object so as to acquire a corresponding plurality of sets of measurement data representative of radiation attenuation caused by said object;

processing the acquired measurement data so as to develop Radon data on a set of vertically oriented co-axial φ-planes that partition a Radon space; and reconstructing an image of the object by performing two 2D radon inversions of the Radon data, wherein each of the Radon space φ-planes is sampled during a first of said inversion processing's so as to have its own independent local Radon origin.

2. The method of claim 1, wherein said two-step Radon inversion processing includes a processing step that compensates for a shift of the local Radon origin of each φ-plane with respect to a global coordinate system.

3. A method of operating a 3D CT imaging apparatus having a cone beam radiation source and detector arrangement, for reconstructing an image of an object that is scanned by said source and detector arrangement, comprising the following steps:

operating said source and detector arrangement at a plurality of source positions along a scan path that traverses the object so as to acquire a corresponding plurality of sets of measurement data representative of radiation attenuation caused by said object;

processing the acquired measurement data so as to develop Radon data on a set of vertically oriented co-axial φ-planes that partition a Radon space, wherein each of the φ-planes is sampled so as to have its own independent local Radon origin; and reconstructing an image of the object by performing two-step 3D Radon inversion processing of the Radon data wherein each of the φ-planes is independently processed.

4. The method of claim 3, wherein said two-step Radon inversion processing includes a first step that compensates for a shift of the local Radon origins with respect to a global coordinate system by backprojecting the Radon data from the φ-planes onto φ-plane sample grids (z,r') which are not shifted, i.e., are accordingly offset, from the local Radon origins.

5. The method of claim 3, wherein said two-step Radon inversion processing includes a first step that compensates for a shift of the local Radon origins with respect to a global coordinate system by backprojecting the Radon data onto φ-plane sample grids (z,r') which are shifted along with the local Radon origins, and then, before performing a second step of the two-step inversion processing, shifting the backprojection results a corresponding amount toward the global origin to compensate for the previous shift in the local Radon origins.

6. The method of claim 4, wherein the backprojecting of the first step includes introducing a corresponding offset into coordinate variables that define the backprojecting.

7. The method of claim 6, wherein the shifting of the backprojection results is accomplished by interpolating the results onto a new grid which is aligned with the global coordinate system.

* * * * *